United States Patent
Besson

(10) Patent No.: US 7,342,993 B2
(45) Date of Patent: Mar. 11, 2008

(54) SYSTEM FOR DYNAMIC LOW DOSE X-RAY IMAGING

(76) Inventor: Guy M. Besson, 1672 Emerald St., Broomfield, CO (US) 80020

( * ) Notice: Subject to any disclaimer, the term of this patent is extended or adjusted under 35 U.S.C. 154(b) by 0 days.

(21) Appl. No.: 11/351,446

(22) Filed: Feb. 10, 2006

(65) Prior Publication Data

US 2006/0182224 A1 Aug. 17, 2006

Related U.S. Application Data

(60) Provisional application No. 60/652,127, filed on Feb. 11, 2005, provisional application No. 60/654,922, filed on Feb. 22, 2005.

(51) Int. Cl.
*G01N 23/00* (2006.01)
*G21K 5/10* (2006.01)

(52) U.S. Cl. .......... 378/19; 378/26; 250/370.1

(58) Field of Classification Search .......... 378/4–27, 378/146; 250/370.08, 370.09
See application file for complete search history.

(56) References Cited

U.S. PATENT DOCUMENTS

| | | | | |
|---|---|---|---|---|
| 4,228,357 | A | * | 10/1980 | Annis .......... 378/62 |
| 4,398,302 | A | * | 8/1983 | Pfeiler .......... 378/146 |
| 4,989,225 | A | * | 1/1991 | Gupta et al. .......... 378/10 |
| 6,950,492 | B2 | | 9/2005 | Besson |
| 7,016,457 | B1 | * | 3/2006 | Senzig et al. .......... 378/19 |
| 2001/0048732 | A1 | * | 12/2001 | Wilson et al. .......... 378/21 |
| 2003/0209662 | A1 | * | 11/2003 | Nelson et al. .......... 250/252.1 |
| 2005/0027194 | A1 | * | 2/2005 | Adler et al. .......... 600/427 |
| 2005/0055174 | A1 | * | 3/2005 | David et al. .......... 702/152 |

OTHER PUBLICATIONS

Besson, G.M., "CT Projection Estimation And Applications To Fast And Local Reconstruction," Proc. SPIE 3661, 1999, pp. 1198-1207.
Schomberg, Hermann and Timmer, Jan, "The Gridding Method For Image Reconstruction By Fourier Transformation," IEEE Transactions On Medical Imaging, vol. 14, No. 9, Sep. 1995, pp. 596-607.

* cited by examiner

*Primary Examiner*—Edward J. Glick
*Assistant Examiner*—Anastasia S. Midkiff
(74) *Attorney, Agent, or Firm*—Lathrop & Gage LC

(57) ABSTRACT

A system for low dose x-ray imaging provides for dynamic generation of an x-ray beam with specific shape, and dynamic tracking of a detector with said beam. The detector is rotatable, and translatable along two orthogonal axes, and may mount with a circular detector tray, the tray rotating around a rotation axis. Specific detector shapes include an elongated rectangular matrix, for example with additional detector cells near the rotation center to provide an increased area of continuous detection. Dynamic low-dose x-ray tomosynthesis or limited-angle tomographic imaging is enabled via simultaneous x-ray tube and detector motions during examination, such as fluoroscopic examination of a human body. Data acquired at multiple projection angles is input to a 3D image reconstruction algorithm that provides a refreshed 3D data set during continuing examination. The system may thus also automatically track a point in three-dimensional space, for example continuously locating the tip of a catheter.

17 Claims, 16 Drawing Sheets

SYSTEM FOR DYNAMIC LOW DOSE X-RAY IMAGING

CROSS-REFERENCE TO RELATED APPLICATION

This application claims benefit of priority to U.S. Provisional Pat. Application No. 60/652,127, filed Feb. 11, 2005, and U.S. Provisional Pat. Application No. 60/654,922, filed Feb. 22, 2005, both of which are incorporated herein by reference.

BACKGROUND

1. Field of the Invention

This disclosure relates to the field of x-ray imaging, and more particularly to the dynamic low-dose imaging of an object or subject with a moving detector, as well as to the dynamic low-dose tomosynthesis and limited-angle tomographic imaging of a subject with a moving detector and a moving x-ray source. Specific applications are in the subfields of fluoroscopy, radiography, and cardiology. Other applications are in the fields of non-destructive testing, homeland security, and animal imaging.

2. Description of the Related Art

A number of interventional procedures utilize x-ray as the preferred imaging modality for intervention planning, guidance, monitoring, and control. Although x-ray imaging systems for this purpose are widely available, prior-art systems and approaches are significantly limited. In particular, prior art interventional imaging poses the major impediments of high subject radiation dose and cumulative physician exposure to radiation. In certain procedures, the subject x-ray dose may be high enough to bum the subject's skin. Furthermore, a significant fraction of experienced radiologists and cardiologists are approaching or have reached their annual or life-time accumulated dose limit, and are therefore prevented from, or limited in, the practice of their skills.

In a typical fluoroscopic procedure, an area detector is used to provide a fairly wide imaging field (typically 6 to 16 inches) at a high refresh rate (30 frames per second, or higher). Over the years, image-intensifier technology has evolved to provide electronic amplification and viewing of images. In general, the x-ray image formed on an input phosphor screen is amplified in intensity by a very large factor, by the electronics of a vacuum envelope within an image intensifier. The bright, but typically reduced-area output image is electronically recorded by a video system, and then displayed to the physician in essentially real time. Recently, a number of vendors have introduced digital detectors with refresh rate and x-ray absorption efficiency comparable to that of the image intensifier. However, these improvements have not resolved the issues of high subject and attendant dosage.

Current technologies are further limited, in part, due to use of large area detectors and large exposure area beams. While a number of systems currently offered provide adjustable field-of-view imaging, a large exposure field is desirable to allow the physician to track the progress of an intervention and to maintain view of specific anatomical landmarks during a procedure. The requirement for a large exposed area translates into high detector costs and the need for a scatter-rejecting Bucky grid, which absorbs about one-half of emitted radiation and thus requires that the applied dose be increased by a factor of two. This adds to the aforementioned high subject and attendant dose; furthermore, the requirement for a large exposed area results in relatively low refresh rates over the entire image. For example, read-out of an entire large area detector, or a large area of such a detector, limits the imaging refresh rate.

Cardiology and neurology interventions, which typically require the insertion of a catheter or similar interventional device in the subject's vasculature, can necessitate continuous or intermittent subject exposures for extended durations, resulting in high x-ray doses. For example, specific cardiology procedures using current, known technologies, such as in electro-physiology, can last for more than one hour, and accordingly necessitate very high subject doses. Interventional radiologists, cardiologists and other attending staff are also subject to significant x-ray exposure and dose, to such a degree that dose limitation regulations may prevent them from active work for a significant fraction of their available time, thus leading to underutilization of expensive resources.

Three-dimensional (3D) imaging currently requires complex and expensive systems. In addition, most currently available 3D imaging systems also deliver high subject doses, and often limit access to the subject due to use of a gantry, a large area detector or a combination of area detectors.

SUMMARY

The methods and system disclosed herein allow for low-dose x-ray examinations as well as dynamic multispectral x-ray imaging in both radiographic and fluoroscopic modes, by translating and rotating a narrow-aperture detector and shaping a beam of x-rays accordingly, or by sweeping or rotating a beam of specific shape across the face of an area detector. Such innovations may facilitate real-time tracking and low-dose imaging of a catheter tip or other object (e.g., a biopsy needle or a surgical tool) inserted in a subject during an interventional procedure, for example as performed in interventional radiography, interventional neurology and interventional cardiology. In a more general sense, the disclosed methods and system facilitate real-time guidance of surgery.

In one embodiment, x-ray examination of a subject or object involves scanning an x-ray fan-beam of specific shape across the subject or object. A detector is mounted on a movable assembly below the subject table, for example on a detector tray. The detector tray enables (a) independent scanning motions in two (preferably orthogonal) directions of a plane or other surface, typically chosen to be parallel to a subject table plane, and (b) independent rotation of the detector. The detector moves simultaneously along these degrees of freedom.

In one embodiment, a method for dynamic x-ray imaging of a subject includes generating an x-ray beam having a non-circular shape about a beam central axis; and irradiating at least part of the subject with the non-circular beam while rotating the non-circular beam about the beam central axis.

In one embodiment, a method for dynamic x-ray imaging of an object or part of an object includes moving a detector tray supporting a detector having a non-circular shape by rotating the detector tray. An x-ray beam is shaped to generally match the shape or part of the shape of the detector. The x-ray beam is moved or oriented to track the motion of the non-circular detector.

A system for dynamic x-ray imaging of an object or part of an object includes a gantry to rotate a detector of non-circular shape, and a collimator to shape an x-ray beam to generally match the shape or part of the shape of the non-circular detector. An included beam orientation mechanism tracks the motion of the non-circular detector with the x-ray beam.

The foregoing embodiments may also serve in dynamic, low-dose x-ray tomosynthesis and limited angle tomographic imaging systems. In a particular embodiment, an x-ray source and a detector of a specific shape are moved simultaneously along a number of motion axes, an x-ray beam from the source tracking location and motion of the detector. Multiple images are taken and may be mathematically processed to image a plurality of slices or horizons through a subject. In another embodiment, the x-ray source and detector may be stationary, while the subject is moved along one or more motion axes. One advantage to this type of tomosynthesis system is that it may be constructed and arranged for operation in a plurality of selectable imaging states including a tomosynthesis state and a non-tomosynthesis state. The use of a rotating collimator and/or rotating detector for low dose imaging permits, for example, the use of a narrow shaped beam in imaging performed as a fluoroscopic system, while also the same system may be operated by different control instructions to provide tomosynthesis.

Still further, the disclosed instrumentalities may be incorporated in multi-spectral imaging systems with or without computer assisted diagnosis (CAD). One example of this would be to retrofit the system that is shown and described in U.S. Pat. No. 6,950,492, which is hereby incorporated by reference to the same extent as though fully disclosed herein. This type of system, for example, may be provided with a rotating collimator assembly as described herein, as well as a rotating detector driven in synchronicity with the collimator assembly.

Other objects and advantages of the present disclosure will become apparent from the following descriptions, taken in connection with the accompanying drawings, wherein, by way of illustration and example, embodiments of the present invention are disclosed.

DETAILED DESCRIPTION

Figure 1A:
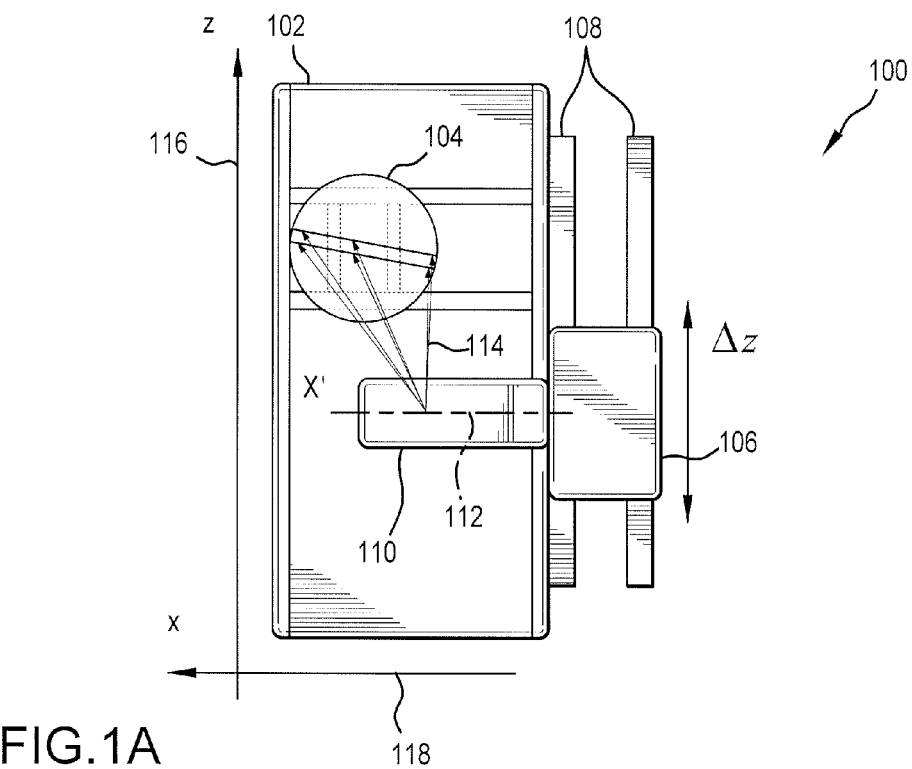
FIG. 1A is a top orthogonal view of a system for dynamic low dose x-ray imaging, including a moveable detector assembly.

Before proceeding with the detailed description, it should be noted that the matter contained in the following description and/or shown in the accompanying drawings may be embodied in various forms, and should therefore be interpreted as illustrative, and not in a limiting sense. Elements shown in the drawings are not necessarily to scale and may be exaggerated, enlarged or simplified, to facilitate understanding of the invention. The system implementation according to the various shown embodiments is amenable to automated controls. These may use circuitry including a controller or driver to interface with a computer. Processing may be accomplished using one or more processing units operably coupled with memory and data storage devices. System operations may be governed by program instructions and/or circuitry. Actuation, as described below, may be accomplished under motive force provided by step motors that are governed by these controls, where such motors are operably coupled with gears or drive belts to accomplished the desired movements. Motive force may alternatively be provided manually, as well as by pneumatic, hydraulic, or magnetic devices.

In one aspect, servo mechanisms may be governed by feedback control to maintain alignment between a shaped beam that is emitted through a collimator and a shaped detector. This is particularly useful in embodiments that utilize a rotating collimator and a rotating detector that move in synchronicity with one another. In one example of this where the detector is slightly oversize relative to the beam, a detector sense signal indicating misalignment may result in the detector and/or the collimator being rotated to restore alignment. Furthermore, the detector sense signal may be interpolated for projection onto a uniform reference grid so that there is no loss of data.

Figure 11:
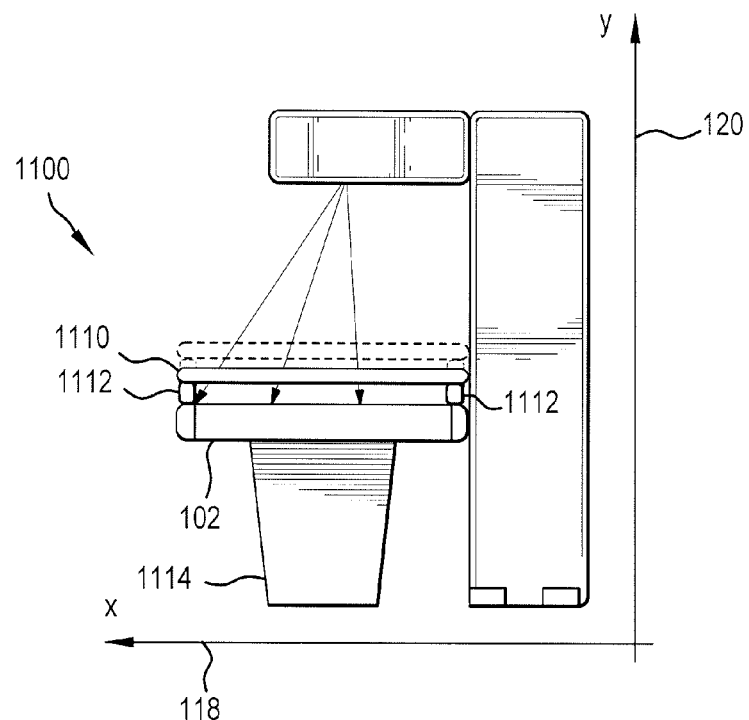
FIG. 11 illustrates a system for dynamic low dose x-ray imaging including a movable subject table, in accordance with one embodiment.

Turning now to FIG. 1A, a system 100 for dynamic low dose x-ray imaging is shown in a top orthogonal view. System 100 for example allows a significant reduction in subject and physician dose while permitting effective performance of an interventional procedure. A frame structure (or cradle) 102, designed for placement beneath or within a subject table (see, e.g., table 1110; FIG. 11), permits relative motion of a detector assembly 104 (shown bounded by a circle) with respect to the table. An x-ray tube apparatus assembly, such as a column or x-ray source assembly having an x-ray tube and a collimator, may for example be set upon rails that allow motion of the assembly in a direction generally parallel to the subject table.

In one embodiment, a tube column assembly 106 is placed on one side of cradle 102 and the subject table, and may be dynamically rolled along rails 108 (or similar translation structure, such as a slide or roller assembly), which are for example parallel to the subject table, during the examination. In one embodiment, an x-ray tube 110 pivots with respect to a pivot axis (x') 112 that lies generally parallel to the subject table (alternatively, image plane x O z). The combination of independent detector motion (relative to a surface that is often chosen to be parallel to the plane of the subject table), tube column translation and tube rotation, together with an adjustable collimator assembly (e.g., assembly 1010, described herein below with respect to FIG. 10), allows projection of an x-ray beam 114 of specific shape towards any area on the subject table.

Figure 1B:
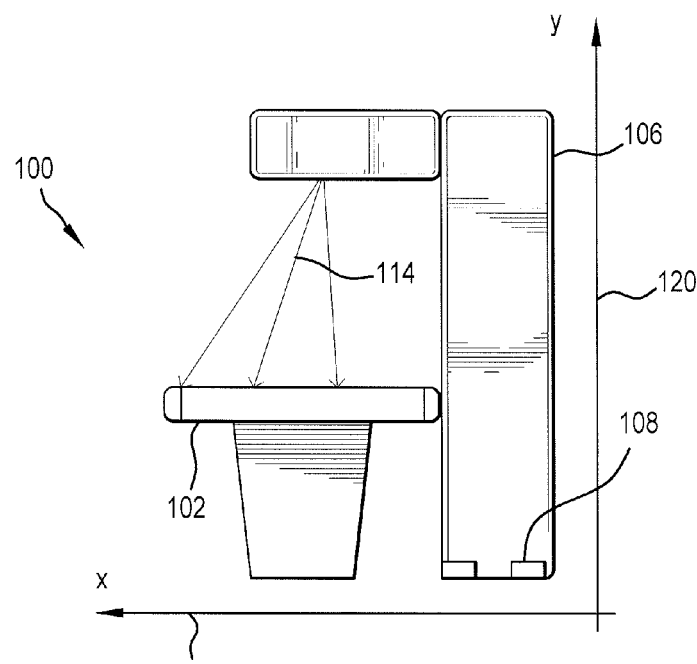
FIG. 1B is a front orthogonal view of the system of FIG. 1A.
Figure 1C:
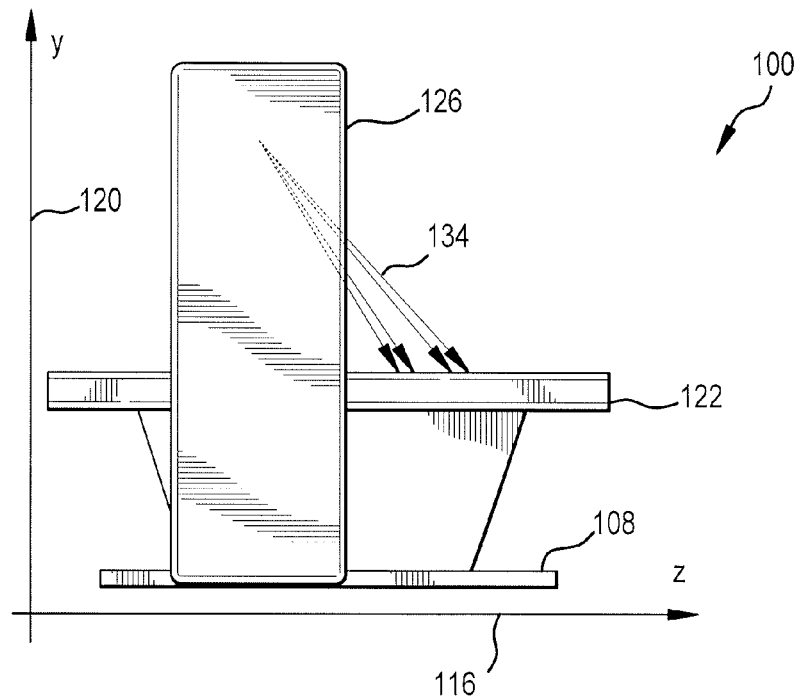
FIG. 1C is a side orthogonal view of the system of FIG. 1A.

FIG. 1B depicts a front view and FIG. 1C depicts a side view of system 100. Combined FIGS. 1A-1C show a longitudinal subject axis (z) 116, a lateral axis (x) 118 and a table-to-source axis (y) 120. Axis y' 122 (shown in FIG. 3) passes through the detector assembly 104 center of rotation and is orthogonal to a detector tray, e.g., rotable tray 204, FIG. 2.

Figure 1D:
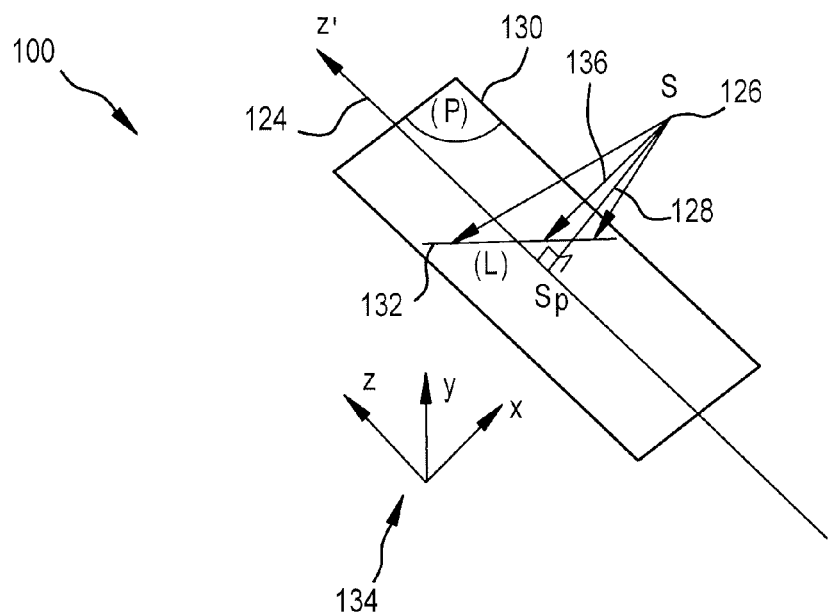
FIG. 1D is a geometric perspective view of the system of FIG. 1A.
Figure 10A:
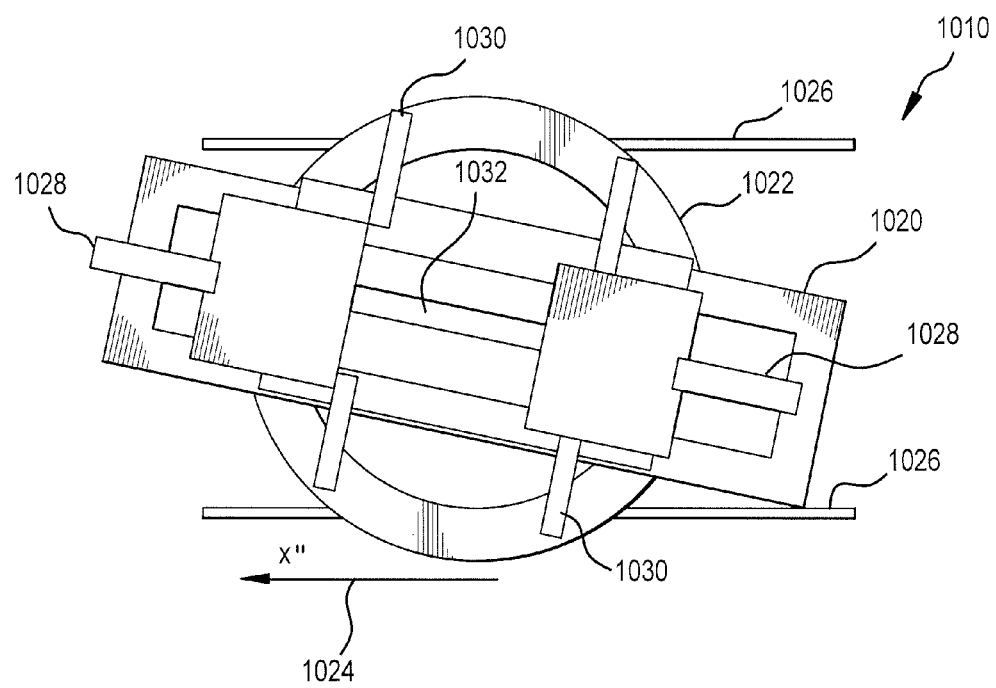
FIG. 10A provides a schematic view of a collimator assembly, in accordance with one embodiment.
Figure 10B:
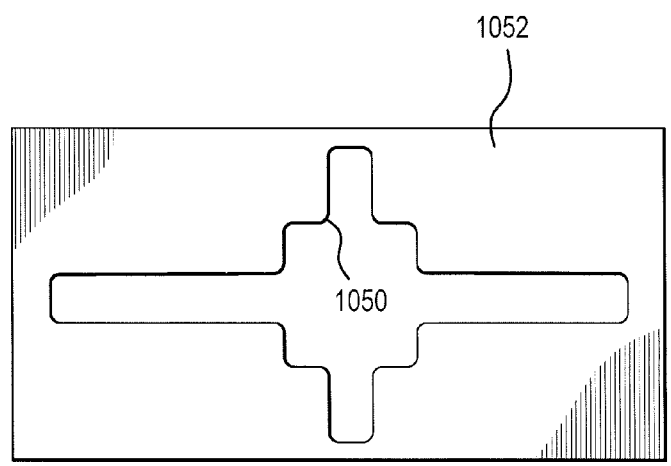
FIG. 10B illustrates adjustment of the shape of the collimator assembly of FIG. 10A, to reflect the arrangement of detector cells shown in FIG. 4B.

FIG. 1D is a perspective view illustrating exemplary geometry of system 100. An object or subject axis z' 124 is for example generally parallel to longitudinal axis 116, and passes through the object or subject's center of gravity. In the case of subject imaging, this axis 124 may be collinear with the subject's main axis of elongation. In the case of inanimate object imaging, the object axis is chosen by convention to be parallel to longitudinal axis 116 and passing through the object's center of gravity. The x-ray source, e.g., projection source (S) 126 is located at a point that does not belong to the chosen object axis, and is retained as defining the vertex of a geometric projection source. A projection direction 128 is then defined as the line passing by the projection source 126 and the object axis 124 and orthogonal to the object axis 124; projection plane 130 is then defined as the plane containing object axis 124 and orthogonal to the projection direction 128. Sp represents the orthogonal projection of source 126 upon plane 130. An x-ray beam as shaped and defined by a collimator assembly, described herein below with respect to FIG. 10, presents at least one defined main direction, corresponding to the most elongated beam dimension as projected onto the projection plane 130. The intersection of the elongate beam axis and projection plane 130 defines a line 132 on the projection plane 130. The aforementioned directions may be determined according to a fixed, or laboratory reference system 134. Further, an x-ray beam shaped and defined by a collimator assembly according to the principles laid out herein presents a beam central axis 136 passing through the source 126 and generally passing through the geometric center of the beam projection in plane 130 or in the plane of detector assembly 104. In practice, such a beam central axis may be chosen to correspond to the rotational axis of a rotating collimator assembly, for example as described herein below with respect to FIGS. 10A-10B and 14. The beam central axis may also be chosen to pass through the detector assembly 104 center of rotation. It is noted that, in general, the beam projection onto plane (P) does not include point $S_p$, nor does the x-ray beam necessarily include projection direction 128.

Figure 2:
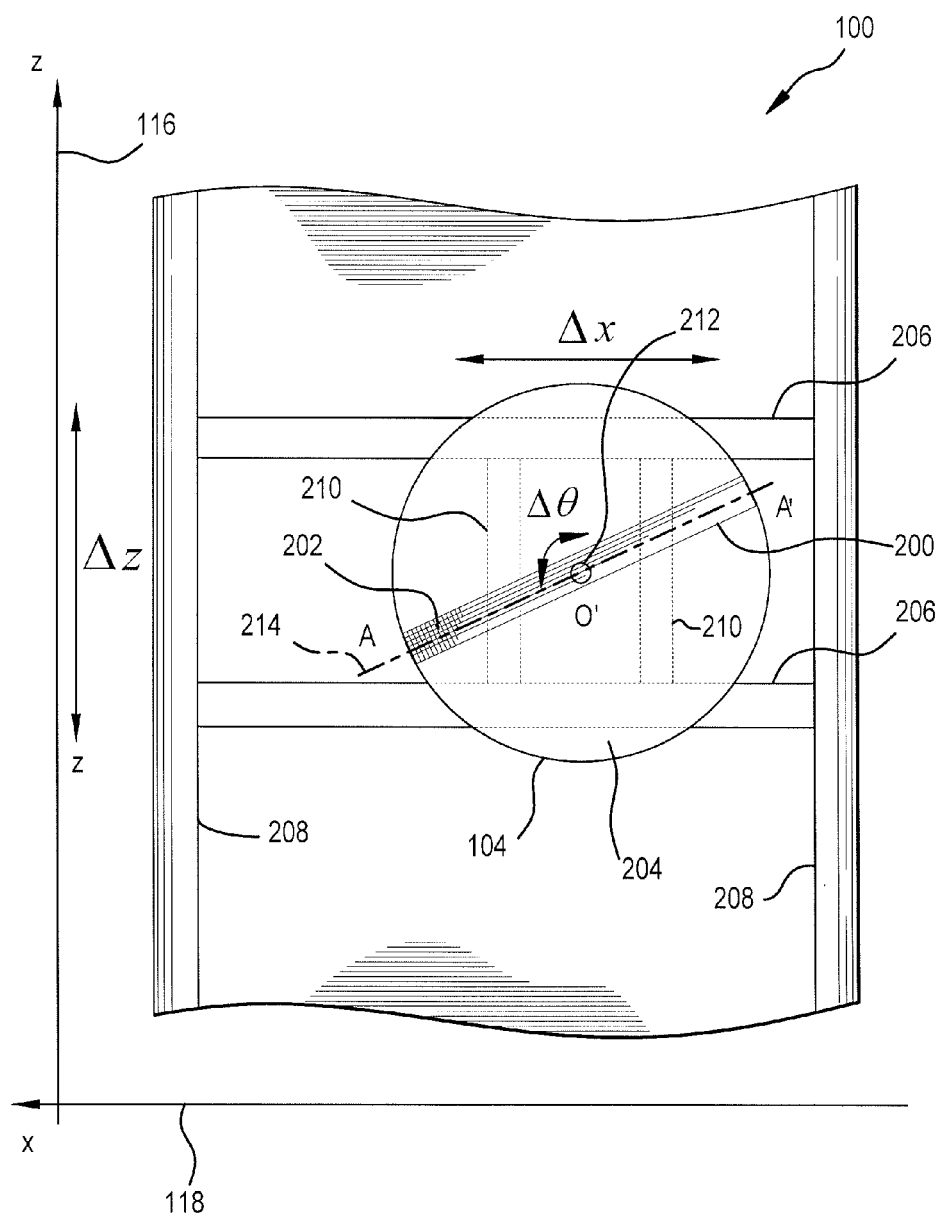
FIG. 2 schematically illustrates the moveable x-ray detector assembly shown in FIGS. 1A-1D.

As shown in FIG. 2, system 100 may provide a fast, full-frame sampling detector assembly, designed according to the principles disclosed herein. Detector assembly 104 for example includes a detector 200 having detector cells 202 arranged as a matrix, shown as having a rectangular shape. Detector 200 may mount on a moveable assembly, such as a detector tray 204, itself assembled on sets of rails 206 and 208 underneath or within a subject examination table (e.g., table 606, FIG. 6), which enable independent motion along two directions x and z. As shown in FIG. 2, detector tray 204 is circular; however, alternate shapes may be utilized in connection with detector 200.

Figure 3:
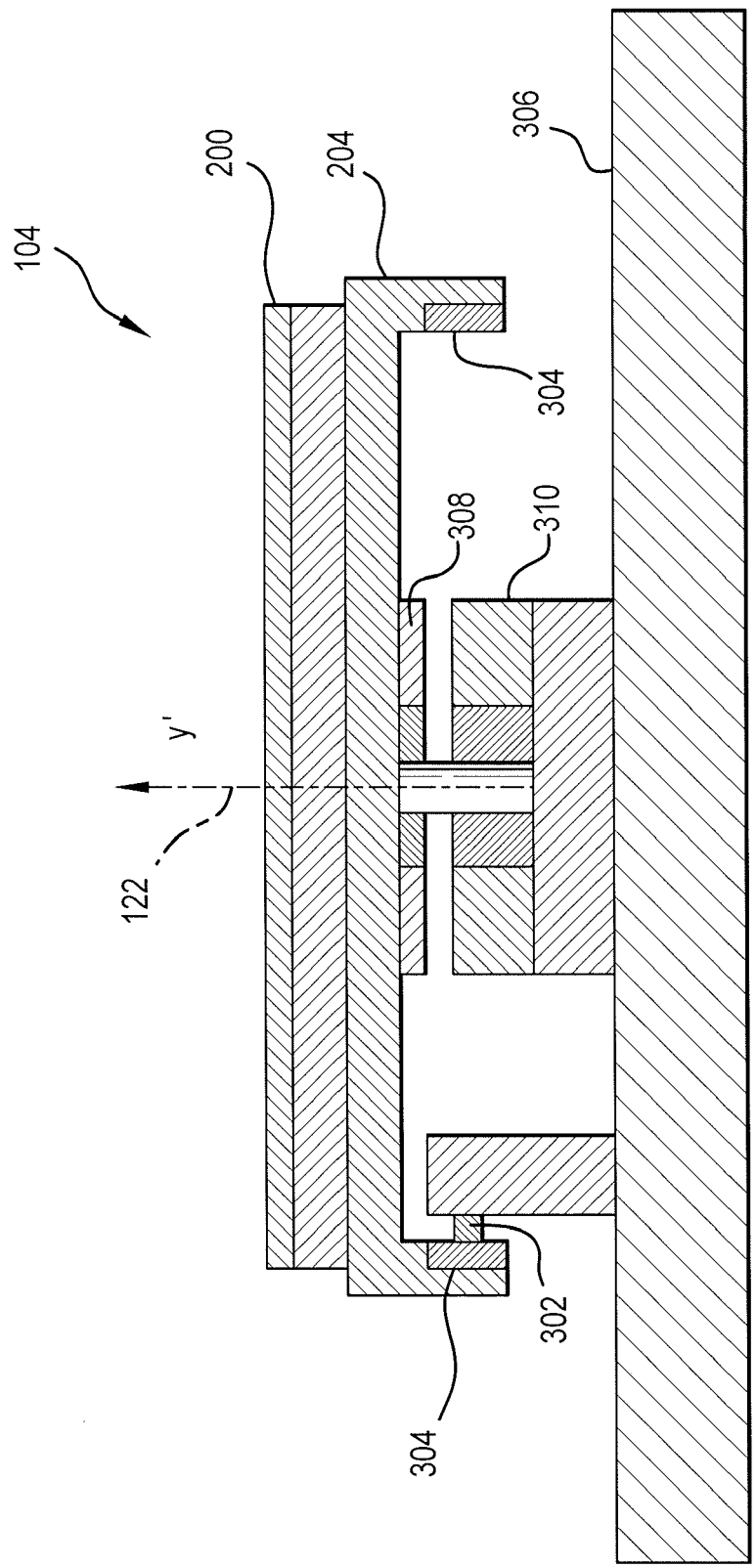
FIG. 3 is a cross-sectional view of a detector tray of the assembly of FIG. 2.

In the embodiment illustrated in FIG. 2, detector tray 204 has three degrees of freedom: (1) translation $\Delta z$ along the longitudinal table/subject axis 116, (2) translation $\Delta x$ along the orthogonal direction 118 in the plane of the subject table, and (3) rotation $\Delta \theta$ with respect to axis y' 122 (see FIG. 3), which is generally orthogonal to the plane of the subject table and generally in the direction of axis 120. These degrees of freedom may be activated independently, in combination, in turn or simultaneously. FIG. 2 illustrates part of the mechanical assembly that enables these motions. Detector tray 204 is mounted on an assembly (illustrated as two beams 210 parallel to axis 116). Beams 210 terminate at a system of wheels or similar translation structure, such as a slide or roller assembly (not shown) that allows motorized translation along rails 206, parallel to x axis 118. Rails 206 also terminate at a system of wheels or similar translation structure, such as a slide or roller assembly (not shown) that rolls on parallel rails 208, oriented parallel to z axis 116. Accordingly, the center or center of rotation O' 212 of detector tray 204 can be juxtaposed with any location within a plane (or upon a surface) that is generally parallel to the subject table, for example, image plane x O z, shown in FIG. 5 (subject to mechanical limitations on excursion ranges), by actuation of motors for translation along rails 206, 210 (motors not shown). Further, as shown in FIG. 3, detector tray 204 is mounted with a rotation axis y' 122 generally orthogonal to a plane that is locally tangent to the detector motion surface or plane (e.g., image plane x O z, FIG. 5). Detector tray 204 may freely rotate around axis 122.

FIG. 3 provides a cross-sectional view of detector assembly 104 along the line AA' 214 of FIG. 2. Line AA' passes through detector center 212 and is parallel to the elongate axis of detector 200, e.g., parallel to a plane including detector cells 202. Power is for example provided to detector 200 via a brush link 302 and a slip-ring 304 assembly, although it is understood that power provision may be accomplished using alternate components. Transmission of detector data between rotating tray 204 and a detector base 306 may be provided by a transmitter and receiver assembly, for example including transmit and receive elements 308, 310, which transmit detector data through radio-frequency (RF) signals. However, other known methods of data transfer, such as brush-link data transfer, may provide data transmission from rotating tray 204 to base 306 (and from base 306 to tray 204).

Detector base 306 is a non-rotating base, for example due to fixed mounting on a non-rotating portion of detector assembly 104. Transmit/receive elements 308, 310 may mount with rotating tray 204 and non-rotating detector base 306, respectively. The above-described combination of features facilitates unimpeded and unlimited rotation of detector tray 204 for any number of clockwise or counter-clockwise revolutions generally in the plane of the detector, and further enables transmission of power and data to and from detector assembly 104. Alternatively, and in other embodiments, detector motions may be restricted to two directions within a plane; or motion may be restricted to a single scan direction, either within a plane or along a curved path.

Figure 4A:
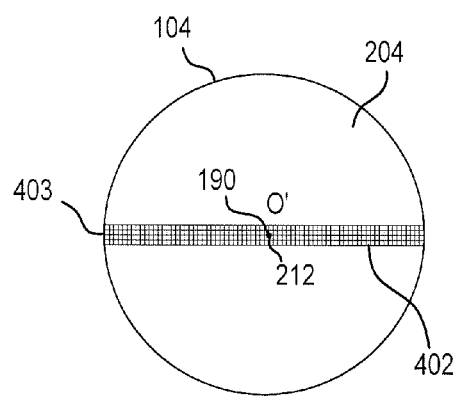
FIG. 4A illustrates a matrix of detector cells, in accordance with one embodiment.

FIGS. 4A-4D illustrate four of a number of possible detector cell arrangements upon detector tray 204. FIG. 4A shows a matrix of detector cells 402 arranged along a slot, as elongated rectangular matrix 403. In one embodiment, detector matrices are designed as a combination of square or rectangular detector modules that can be tiled along any dimension in a plane or surface. Current detector technologies allow design of such modules, possibly including backplane read-out; with such an arrangement, the spacing or gap between adjacent detector modules can be reduced to a dimension less than or equal to that of the detector cell pitch.

Figure 4B:
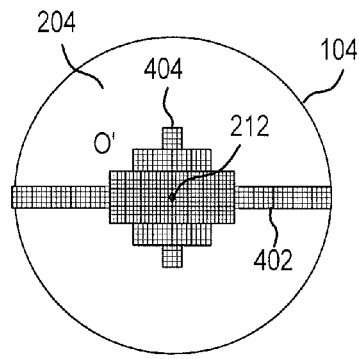
FIG. 4B shows the matrix of FIG. 4A, with an arrangement of detector modules.

FIG. 4A also shows the intersection 190 of an x-ray beam (not shown) central axis with the plane (e.g., image plane x O z, FIG. 5) of detector assembly 104. FIG. 4B shows rectangular matrix 403 of FIG. 4A with additional detector modules 404 provided near center of rotation 212. Such an arrangement, when properly matched by a source-collimator assembly, may provide effective trade-offs between the amount of area that is under continuous x-ray exposure and the areas more distal from center of rotation 212, which are exposed only twice for each full rotation of detector tray 204.

Figure 4C:
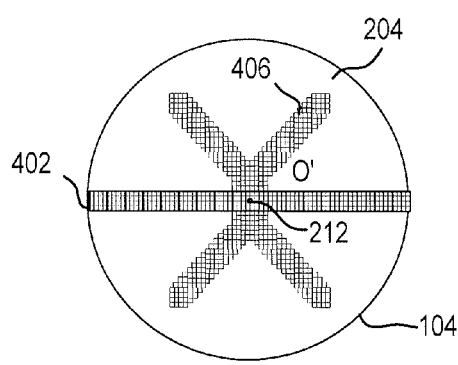
FIG. 4C shows the matrix of FIG. 4A, with a alternate arrangement of detector modules.
Figure 4D:
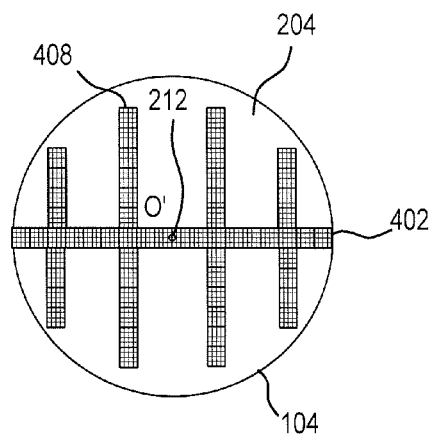
FIG. 4D illustrates the matrix of FIG. 4A, with another alternate arrangement of detector modules.

As shown in FIG. 4C, alternate (or additional) detector module arrays 406 may be provided. Arrays 406 for example have various widths, lengths and detector cell sizes, along with other variable design parameters, and may be generally arranged along a plurality of radial lines passing through center of rotation 212. FIG. 4D illustrates the use of four additional detector module arrays 408 arranged as lines that are for example matched to a multi-slot collimator assembly. Many other arrangements of module arrays 408, such as areas of varying widths, lengths and detector cell resolution, are possible and may be designed to optimize specific performance.

The fast, full-frame sampling detector allows refresh of the part of an image disk, such as a portion of the fixed image grid that is covered by tray 204, that is spatially coincident with a rotating detector at various rates. In one example of this, areas near rotation axis 122 may be refreshed at the intrinsic detector sample rate, while areas toward the periphery of the disk can be refreshed at a rate that is a function of detector sample rate, detector angular velocity, and detector cell arrangement. This flexibility facilitates relatively slow refresh of the outer part of an image, while faster refresh is provided at and near the image center, thus achieving an overall reduction in dose.

In an interventional procedure using a catheter, for example, the faster refresh at the image center allows a physician to focus clearly on the catheter tip. The refresh rate at the image periphery is for example sufficient to provide landmark data for navigation, while still reducing overall dose to the patient, physician and any attending staff. Dose is reduced because at any given time, a much smaller total area is exposed to radiation as compared with conventional fluoroscopy procedures. Further, as a Bucky grid is not necessary when using a beam covering a reduced area, another two-fold dose reduction may be realized because the delivered dose does not have to be increased to compensate for Bucky grid absorption.

An x-ray source filter (not shown) can be shaped to provide proportionally increased flux towards the extremities of the detector matrix (e.g., detector matrix 403) so that upon continuous rotation, the x-ray dose to various areas of an image disk can be further modulated, by design. In such an embodiment, the filter, located on the tube side of the imaging chain, provides more x-ray attenuation at the image center, and gradually less attenuation towards the side ends of the x-ray beam. Alternatively, the filter may be made of materials with essentially uniform attenuation properties. In other embodiments, such as those employing a plurality of detector lines or areas, the filter can be designed to essentially match the detector shape. Furthermore, different filter properties may be used for each of the corresponding detector areas or lines, therefore providing for simultaneous multi-spectral imaging. In a simple example with a detector array comprising two orthogonal rectangular cell arrays, one of the rectangular detector areas could be illuminated by a high energy beam, while the second rectangular area would be imaged by a low energy beam.

Figure 5:
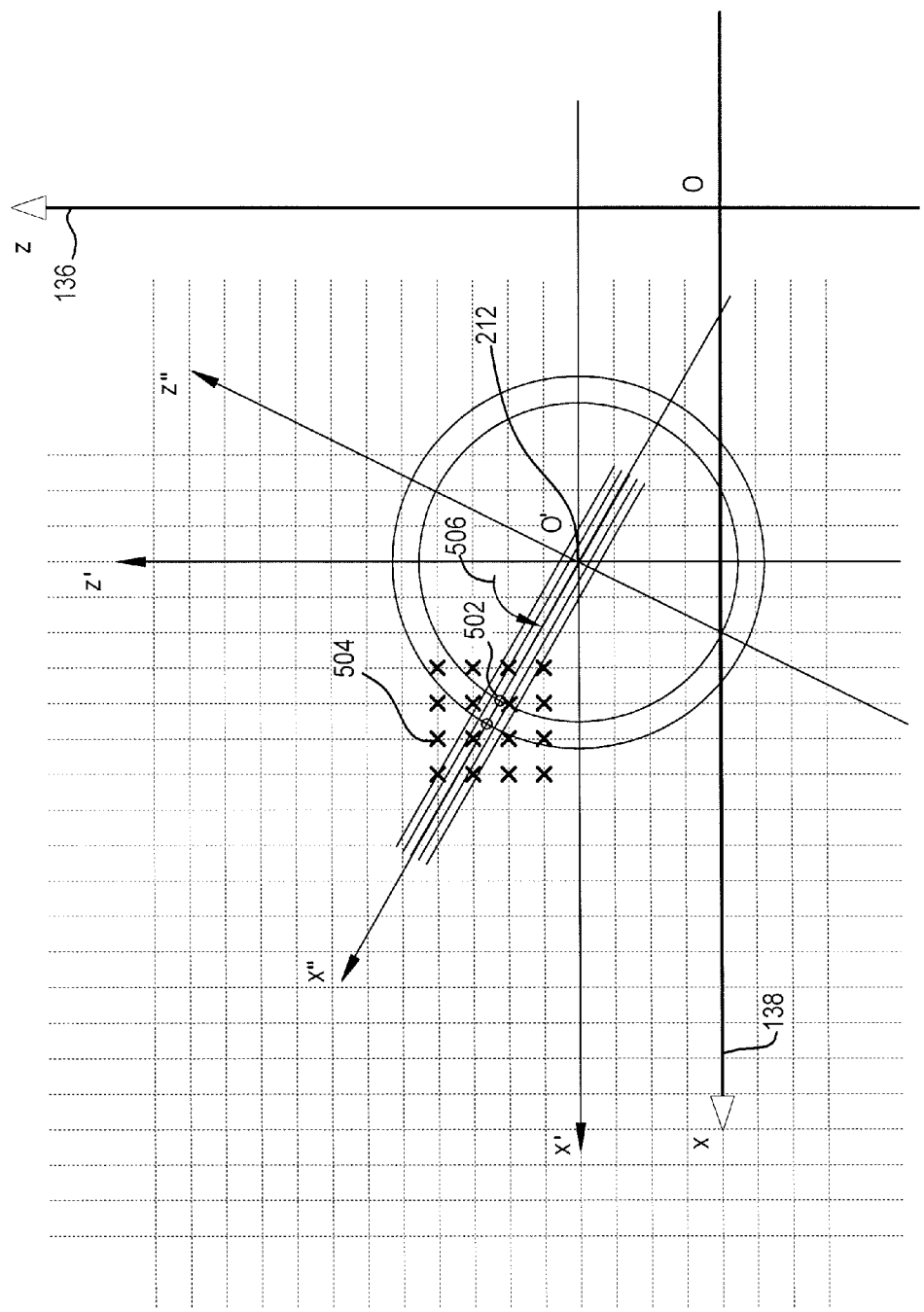
FIG. 5 is a grid illustrating the relationship between x-ray detector samples and image grid points, in accordance with one embodiment.

FIG. 5 illustrates the relationship between detector samples 502 and image grid points 504. In a general case, a given detector sample contributes to a number of image grid samples in a local neighborhood. A number of algorithms have been described, such as the "gridding" algorithm first used in astronomy, that allow efficient interpolation and distribution of the detector samples to the image grid samples. As is seen from FIG. 5, in a general case, center of rotation 212 corresponds to the origin of the referential (x" O z") associated with the moving detector. The origin may be on any point with respect to the table or image plane (x O z), and rotation angle θ 506 may take any value.

Figure 6:
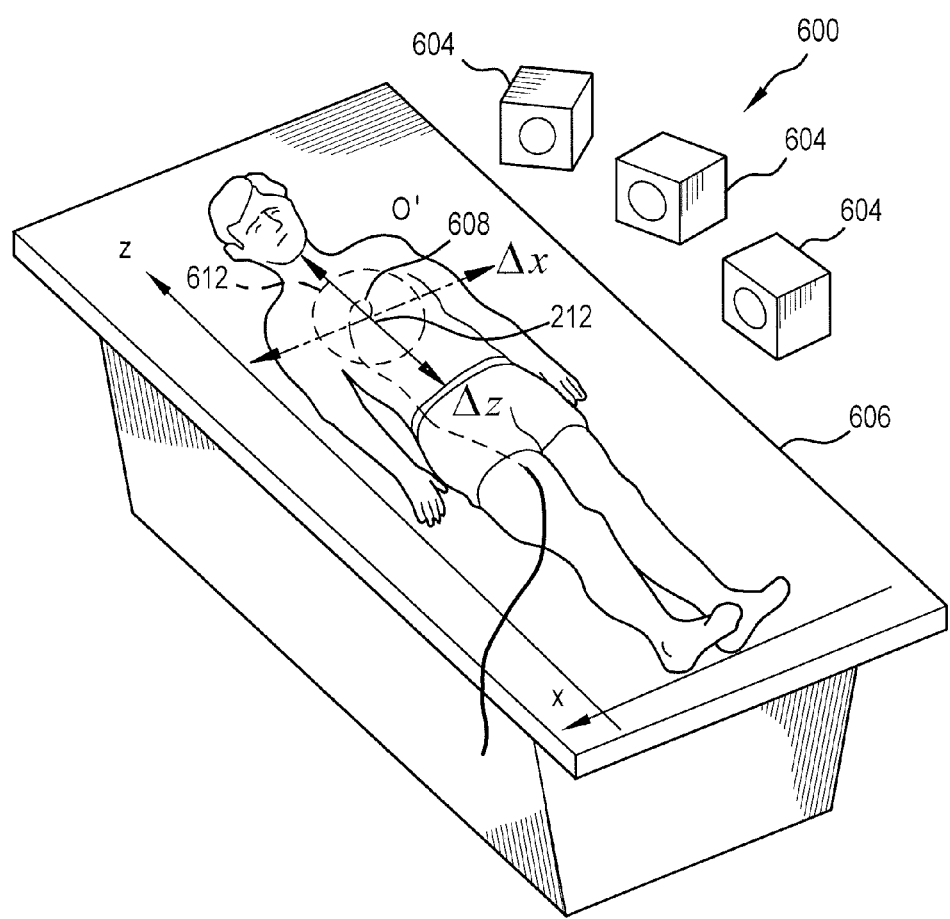
FIG. 6 illustrates the use of a dynamic, low-dose x-ray imaging system with real-time interventional device localization, in accordance with one embodiment.

FIG. 6 illustrates the use of a real-time interventional device localization system 600 together with the dynamic x-ray system described herein above. In one embodiment, three radio-frequency emitters/receivers 604 (not to scale) are placed adjacent a subject table 606 and in such an arrangement as to provide sufficient signal separation for accurate three-dimensional device tip localization. A small assembly 608, for example having three coils, is contained within a device tip (which is for example within region of interest 612, shown bounded by a dotted circle). Analysis of the signals thus received at one or a multiplicity of frequencies permits accurate, real-time localization of the device tip with respect to the table coordinate system, as known in the art. This localization information is fed-back in real-time to the dynamic x-ray imaging system (e.g., system 100), and adjustments are dynamically made to the detector tray position (e.g., tray 204 position), x-ray tube column position (e.g., column 106 position), x-ray tube angle (e.g., tube 110 angle), and x-ray collimator assembly position (e.g., assembly 1010 position), as necessary to track the progress of the device tip with a detected x-ray beam.

Further adjustments to detector raster mode, location and rotation may be made as necessary to enable dynamic tracking of the device tip. Scanning modes include translation of the detector along either the direction parallel to or the direction orthogonal to the short axis of the detector cell matrix (e.g., in directions z" or x" of FIG. 5); combinations of parallel and orthogonal translations; rotation of the detector with respect to center of rotation axis 122, and combinations of rotation and translation motions of the detector tray within the plane of the detector assembly.

In a specific imaging mode, and for illustration, it might be desirable to ensure that the center 212 of detector tray 204 is always positioned with respect to table 606 and the system x-ray tube (e.g., tube 110) in such a manner that the x-ray shadow of the device tip projects onto center 212. Tracking may rely on automatic device tip detection in the projection image, motion of the detector assembly and/or motions of the x-ray imaging chain. A dynamic fluoroscopic image is obtained by simultaneously rotating tray 204 with respect to its instantaneous center, rotating the collimator assembly in synchronicity with the rotating tray 204, and/or translating and/or rotating the collimator across the x-ray port and/or rotating the x-ray tube, for acquiring x-ray data. Synchronicity between the tray and the collimator may be provided mechanically, by design, or through a feedback loop and sensing of relative motion of the x-ray beam with respect to the detector, for example feedback from pixels radiated by the beam penumbra may indicate misalignment between the tray and collimator.

Other applications and modes of implementation are also possible. X-ray data acquisition may be performed in either a pulsed or a continuous mode. In addition, other device or object localization systems or instruments may be employed with system 100.

Figure 7:
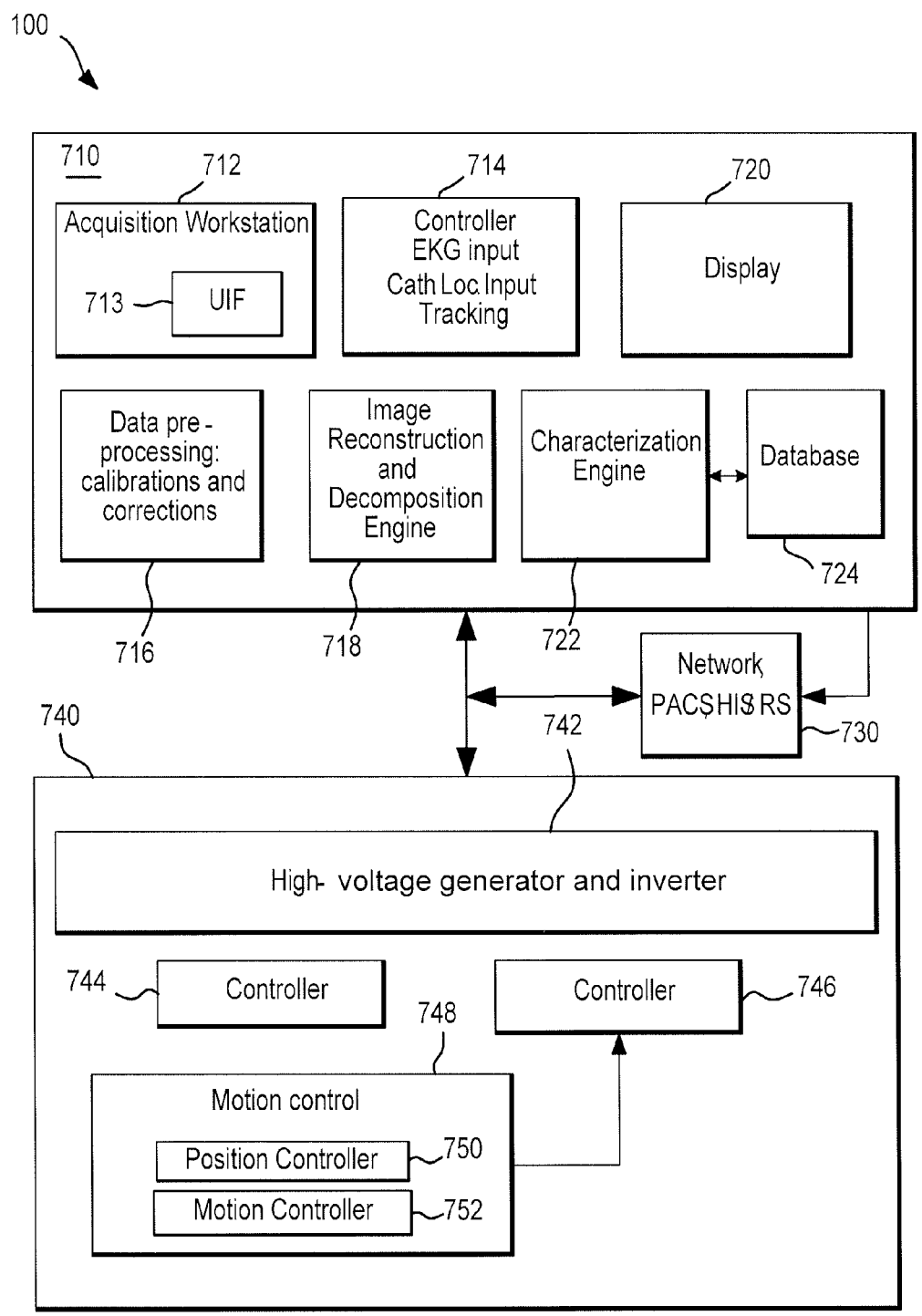
FIG. 7 is a block diagram showing one embodiment of a system for dynamic low dose x-ray imaging.

FIG. 7 presents a block diagram showing system components. The system comprises an image acquisition and review workstation 710, an interface to an hospital or imaging network 730, and a gantry 740. The image acquisition and review workstation 710 has an acquisition workstation 712 with a graphical user interface (UIF) 713; a controller 714 which receives inputs from external devices such as an EKG and/or a device localization system, and drives x-ray emission, acquisition, system motions, and tracking; a data-preprocessing computer architecture 716 for data calibrations and corrections; an image reconstruction and decomposition engine 718; an image display 720; and, for specific application, a feature detection and characterization engine 722 interfacing to a database 724.

The gantry 740 includes: a high-voltage generator and inverter 742 for the generation of time-varying kVp and mA waveforms; a controller 744 for the selection of an anode track and control of x-ray sources and x-ray focal spot parameters (the selection and control of which may vary as a function of time); a controller 746 for the activation of x-ray filters and collimation devices (such action also variable as a function of time); a motion control architecture 748 which itself comprises a controller 750 for the subject, detector cradle, and x-ray tube column positioning and a controller 752 for the motions of the detector assembly (e.g., along z, x axes 118, 116 and rotation Δθ about axis 122).

Figure 8:
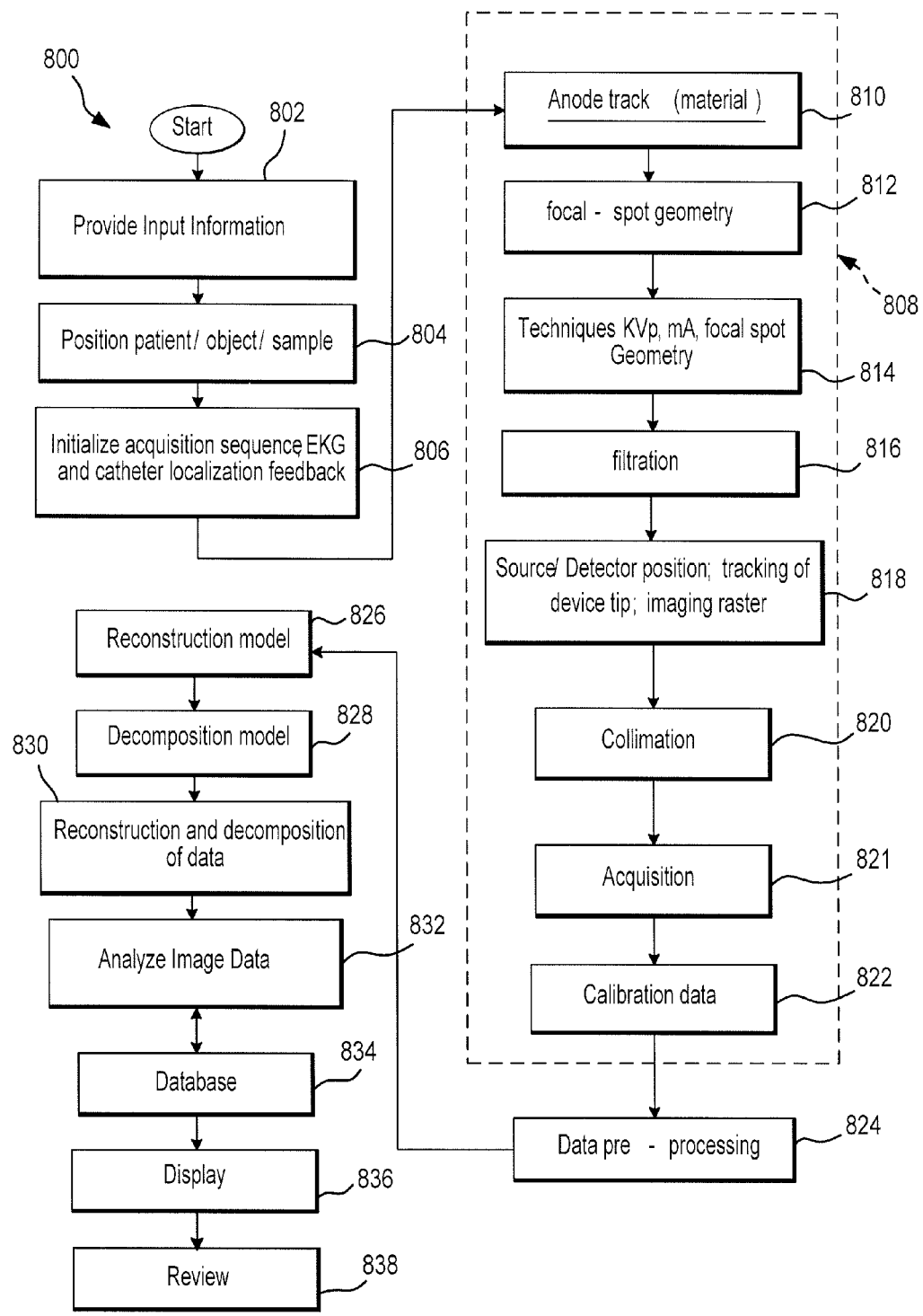
FIG. 8 is a flow chart illustrating data acquisition in a method for dynamic low dose x-ray imaging, in accordance with one embodiment.

FIG. 8 shows an exemplary data acquisition sequence 800. Following startup of the sequence, the user provides input information relating to the subject/object to be imaged, and type of data acquisition sequence to be performed, in step 802. Step 802 for example includes selection of acquisition parameters and input of body information at graphical UIF 713, of FIG. 7. The subject/object is then positioned, in step 804. The acquisition sequence and EKG and device localization feedback are initialized in step 806. Feedback from an EKG and/or feedback from device localization inputs may occur in essentially real time, or data acquisition may proceed according to a pre-determined imaging sequence.

The synchronized acquisition sequence (indicated by dotted box 808) controls selection of spectra, including selection of: an anode track, in step 810; a focal spot geometry, in step 812; x-ray techniques, for example selection of KVp or mA waveforms, in step 814, and filtration, in step 816. The x-ray source and detector assembly are set in motion, in step 818, for example to perform a specific series of image acquisition sequence, to generate a particular imaging raster, or to dynamically track an interventional device tip such as a catheter, sheath, guide wire or other interventional object such as a biopsy needle or a radiation seed implant, e.g., in brachytherapy applications. Collimator controls are activated to dynamically track the detector location and orientation or to perform a specified acquisition sequence, in step 820. Collimator controls are for example activated as a function of body position of a subject upon a subject table, and/or other acquisition parameters. Data is acquired, in step 821, and calibration data is gathered, in step 822. Acquired data (gathered in step 821) is pre-processed, using the calibration data, in step 824. Calibrations and pre-processing is for example performed by computer architecture 716.

An image reconstruction model is generated, in step 826, and an image decomposition model is generated, in step 828. Image reconstruction and decomposition is performed using the reconstruction and decomposition models of steps 826, 828, for example by image reconstruction and decomposition engine 718, in step 830. As may be desirable, the image data are automatically analyzed by a CAD engine, in step 832. The CAD engine, e.g., characterization engine 722, for example provides automatic detection, characterization, and classification of features by data processing and/or by accessing a database, in step 834. Acquired images are then displayed, in step 836, and reviewed, in step 838. A user for example provides inputs via UIF 713 as necessary, for image review.

Figure 9:
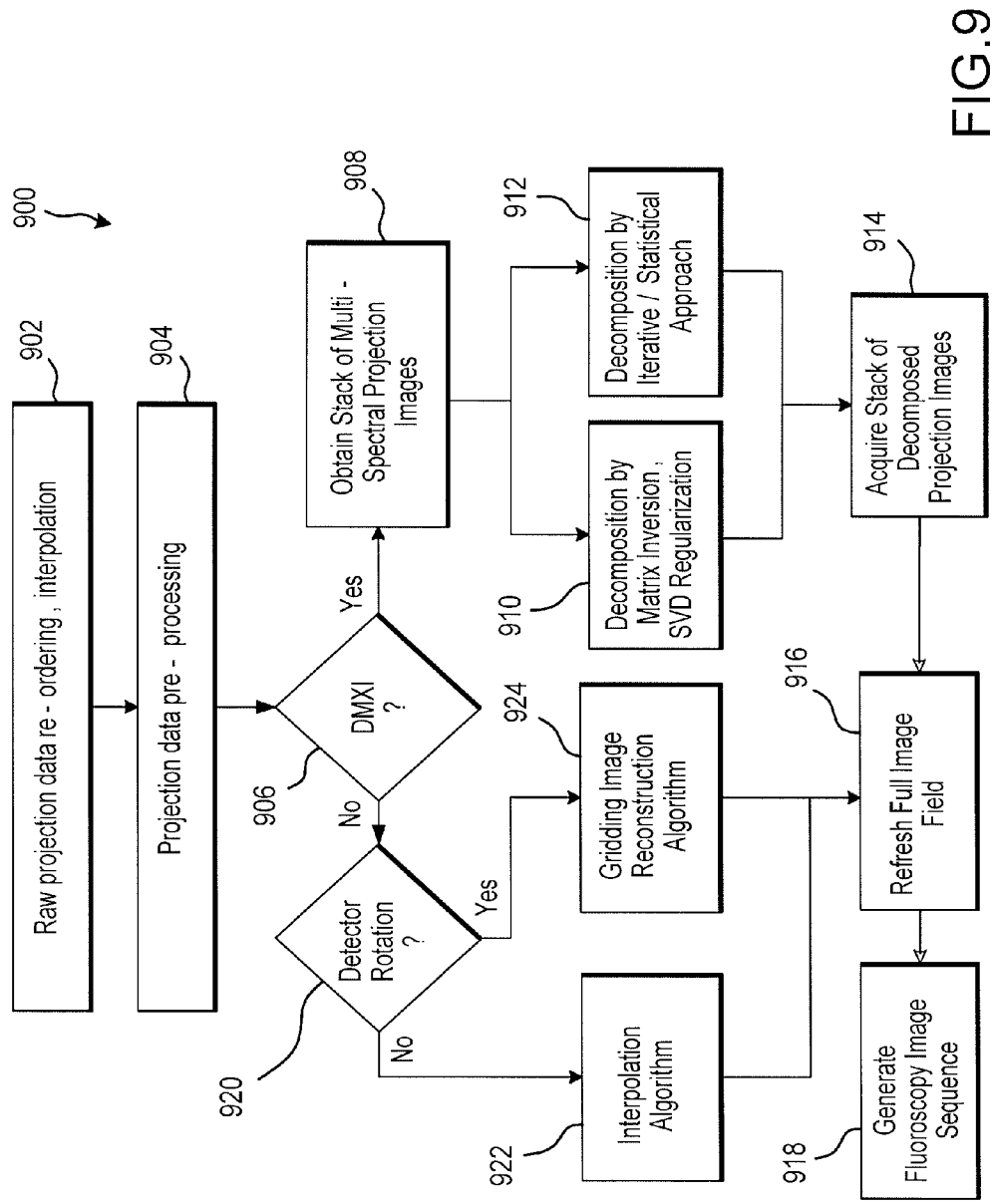
FIG. 9 is a flow chart illustrating image processing and reconstruction in a method for dynamic low dose x-ray imaging, in accordance with one embodiment.

FIG. 9 details a method 900 for image reconstruction using an image reconstruction algorithm, e.g., as performed by engine 718, FIG. 7. Raw projection data are re-ordered and interpolated (if necessary depending on the specifics of the data acquisition sequence), in step 902. Following pre-processing of projection data, in step 904, the algorithm proceeds to image generation. Image generation commences with a determination of whether or not dynamic multispectral x-ray imaging (DXMI) is used, decision 906. In the case of a DMXI image acquisition sequence, a stack of multispectral projection images is obtained, in step 908. These images are decomposed using either a matrix inversion approach, step 910, or an iterative approach, step 912. A stack of decomposed projection images is acquired (via step 910 or 912), in step 914. The acquired images are then used to refresh the full field image, in step 916, thus providing a fluoroscopy or radiography image sequence, step 918.

Alternatively, when DMXI is not used according to decision 906, a further case differentiation is made depending upon rotation of the detector tray, in decision 920. If the detector tray is not rotating, but translating (with the detector tray in an arbitrary angle), various simpler interpolation algorithms may be employed to dynamically build and refresh the full field image, e.g., by interpolating the detector raster to image grid, in step 922. The full field image is refreshed, step 916, and the fluoroscopic or radiographic image sequence generated, in step 918. Alternately, if the detector tray is rotating, decision 920, a more complex interpolation algorithm, such as a gridding algorithm, is employed, in step 924, for image field refresh, step 916, and generation of a fluoroscopic or radiographic image sequence, step 918. The choice of x-ray techniques as well as image frame rate contributes to the distinction between fluoroscopic and radiographic sequences.

FIG. 10A schematically shows one embodiment of a collimator assembly 1010. A collimator 1020 is mounted on a rotatable ring 1022. Such ring can also be translated along an axis x" 1024, by rolling along two rails 1026 parallel to x". A system of collimator blades such as independently adjustable sets of blades 1028 and 1030 mount with the rotatable part of the collimator. Collimator blades 1028 and 1030 open or close along their respective axes, for example to effect an aperture 1032 and an aperture 1032 location that allow a narrow x-ray beam to be generated and to project onto a detector (e.g., detector assembly 104) for any position and/or orientation of the detector. A beam of specific shape, such as a beam including a number of fans (with or without a central wide area), may also be defined by blades 1028 and 1030 as subjected to suitable modifications (not shown). The shaped beam is then translated or rotated across the face of a large area detector or in synchronicity with the motion of a detector of specific shape.

In one embodiment, the shape of the x-ray beam is adjusted to reflect a specific arrangement of detector cells. FIG. 10B shows an aperture 1050 shaped to match the arrangement of cells 402, 404 in FIG. 4B. Aperture 1050 is defined for example by an aperture plate 1052; however, aperture 1050 may also be defined by combining plate 1052 with blades 1028, 1030. Aperture 1050 size and shape may thus be controlled by any one of blades 1028, blades 1030 and aperture plate 1052, or by any combination of blades 1028, 1030 and plate 1052.

To allow a continuous rotation mode, power is provided to the rotatable part of collimator assembly 1010, for example through a slip-ring and brush design (see, e.g., brush link 302 and a slip-ring 304 assembly, FIG. 3). Collimator assembly 1010 includes a filter (not shown), which may include filter materials of various attenuation and x-ray energy filtration properties. In one embodiment, filter attenuation varies from the center to the sides of collimator 1020; in another embodiment, different filters may be provided for each of the different areas of the collimator aperture 1050. Simplified collimator embodiments are also provided by use of an aperture plate 1052, providing for beam formation in a shape matching that of the detector cells such that variations in the projection imaging geometry during an imaging sequence are accounted for. For example, plate 1052 may ensure that a maximum beam width remains less than the width of the associated active detector array. The combination of x-ray aperture, collimator and filter shapes the x-ray beam both spatially and spectrally, as is known in the art. Shaping may also be accomplished using only an aperture and a filter, a collimator and a filter, or a lone collimator.

Dynamically adjustable blades 1028, 1030 may provide a beam of specific width that in typical operation always projects onto the x-ray detector. Further, the width and position of the x-ray beam with respect to the detector matrix may be dynamically adjusted during the image acquisition sequence. This width adjustment, in particular, provides further control of the x-ray dose and noise properties of the image. Analysis of the full-frame data enables tracking of the beam umbra and penumbra onto the active detector. The location and orientation of the beam with respect to the detector as a function of time, for example, allows computerized, automatic prediction of necessary imaging chain (x-ray tube, collimator, detector) adjustments to either track the detector for a given imaging sequence, and/or to track a moving point such as the tip of an interventional device.

Accordingly, detector motion may be tracked in real time based on detected x-ray profile information and/or instantaneous detector coordinate information. Tracking is for example achieved by a combination of the following motions: relative advance of the subject table with respect to the x-ray column, either by table motion or x-ray column motion; x-ray tube pivoting; collimator translations, for example along pivot axis 112, FIG. 1A and/or along an axis generally orthogonal to axis 112 (not shown); collimator rotation, and collimator blades adjustment (both with respect to the width and length of the collimator-defined aperture). In one embodiment, a specific raster and rotation sequence is programmed into both the detector tray controls and into the x-ray tube and collimator assembly controls.

By these instrumentalities, the x-ray beam is spatially shaped to match at least part of the moving detector, in the sense that part of the active detector is illuminated by the beam umbra (largest intensity), and the beam penumbra (or area of drop in intensity) is also imaged by the active detector. For a detector of given shape, the collimator may be adjusted such that the x-ray beam illuminates only part of the detector. For example, if a detector has an elongated array with additional cells along a second, generally elongated array, the collimator may be adjusted such that the x-ray beam illuminates only one of the two elongated arrays. Many other geometries are possible for both the detector and the collimator, as guided by the choice of x-ray imaging sequence and application type.

FIG. 11 illustrates one embodiment of a system 1100 for dynamic, low-dose x-ray imaging utilizing an additional degree of freedom. A subject-supporting table 1110 is adjustable via mechanical actuators 1112, allowing positioning of table 1110 with respect to detector cradle 102. This feature provides for variable geometry and variable magnification of a subject onto a detector plane. Both cradle 102 and subject table 1110 elevation along axis 120 can be adjusted via a cradle support 1114 and corresponding actuators (not shown).

Figure 12:
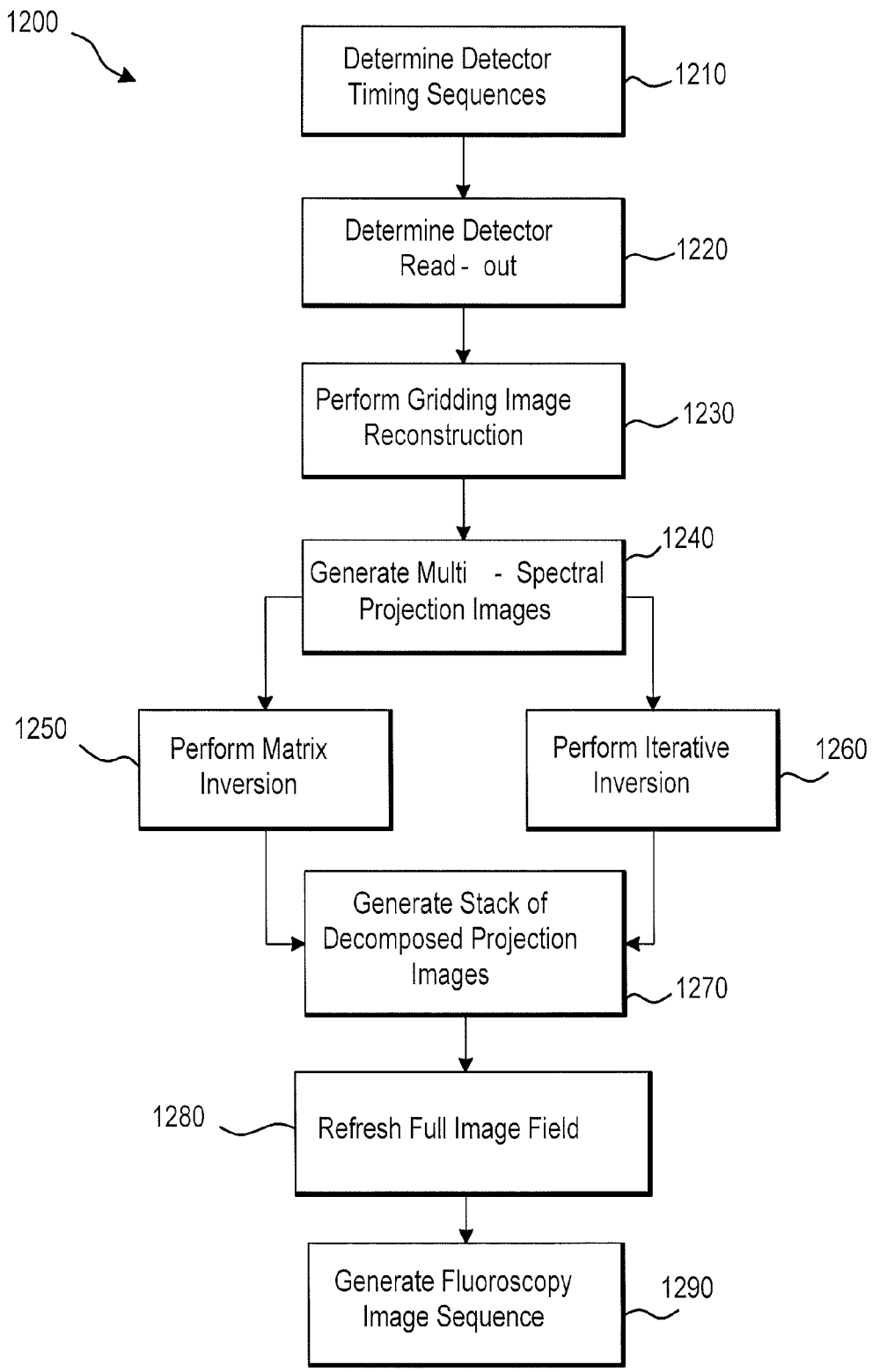
FIG. 12 is a flow chart illustrating an image acquisition sequence of a method for dynamic low dose x-ray imaging, in accordance with one embodiment.

In one embodied image acquisition mode, both dynamic multi-spectral x-ray imaging (DMXI) acquisition and detector tray rotation occur simultaneously. FIG. 12 illustrates a corresponding method for image acquisition. Method 1200 is for example governed by an image acquisition algorithm. Each array or array cell may be subject to variable timing, depending on the specifics of a given acquisition sequence as well as location within the detector. Such variable timing may include both offsets and sample times. Thus, detector timing sequences are determined, in step 1210. Data read-out for each column of the utilized detector array is independently determined, based on image acquisition sequence parameters and detector rotation, in step 1220. Gridding image reconstruction (or similar interpolation method) is performed for the acquired frames, in step 1230. A stack of multispectral projection images is generated, in step 1240. These projection images are input to a decomposition algorithm that performs either a matrix inversion or similar analytical decomposition (e.g., SVD regularization), in step 1250, or an iterative inversion, in step 1260. Accordingly, a stack of decomposed projection images is generated, in step 1270. The acquired decomposed images are then used to refresh the full field image, in step 1280, and to generate a fluoroscopy or radiography image sequence, in step 1290.

Figure 13:
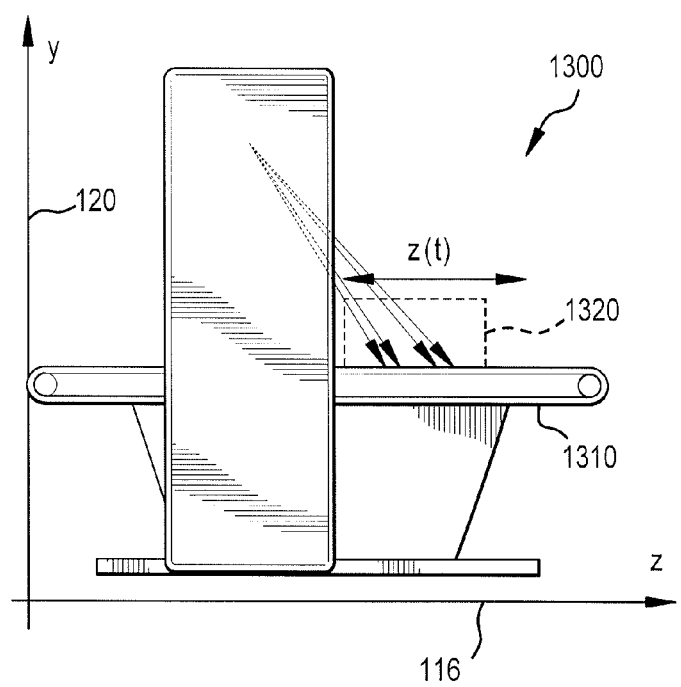
FIG. 13 illustrates parcel or container imaging with a system for dynamic low dose x-ray imaging.

FIG. 13 illustrates use of a system for dynamic, low-dose x-ray imaging for imaging of parcels, inspection of parts, imaging of containers and the like. In one embodiment, system 1300 includes a conveyor belt 1310 for transporting a parcel 1320 to be imaged. Acquisition of a multiplicity of projections of the same object may be facilitated by simultaneous translation of the x-ray tube column along, for example, z axis 116.

Figure 14A:
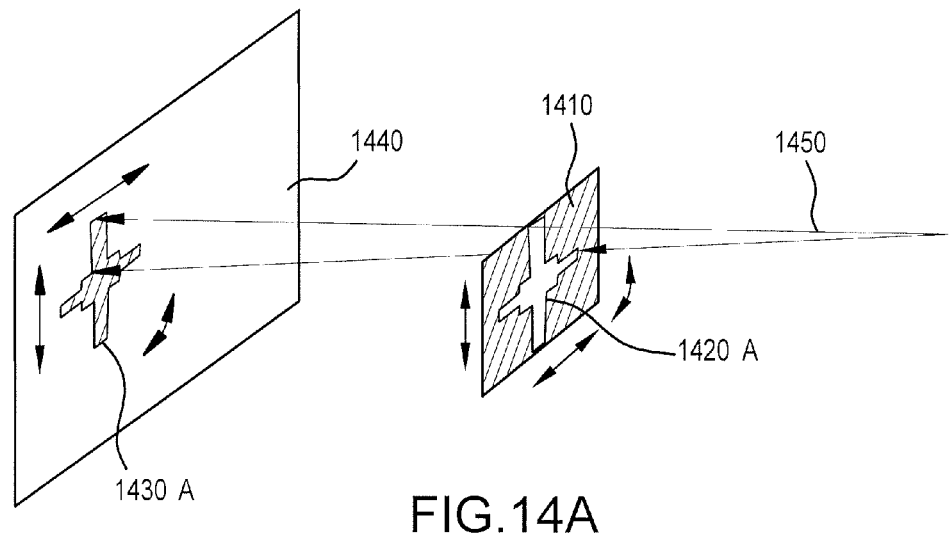
FIG. 14A shows a collimator aperture for use in projecting an x-ray beam of a specific shape onto an x-ray detector, in accordance with one embodiment.
Figure 14B:
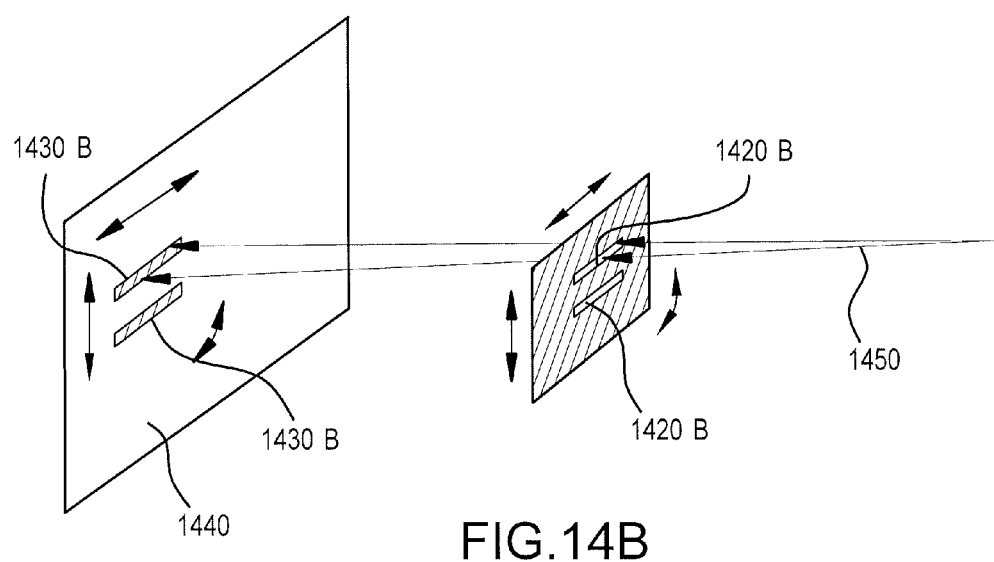
FIG. 14B shows a collimator aperture for use in projecting an x-ray bean of another specific shape onto an x-ray detector, in accordance with one embodiment.

FIGS. 14A-14B depict a collimator assembly 1410 with collimator apertures 1420A, 1420B and collimator blades (not shown), shapes a beam to a specific shape 143 OA, 1430B as projected onto a detector 1440. The beam 1450 is scanned and/or rotated across the face of detector 1440, which is for example a two-dimensional detector. Data is read out of detector 1440 either in a raster fashion or, as possible with newer technologies such as CMOS design, read-out of pre-determined areas in a specific sequence. FIGS. 14A and 14B present two embodiments for two specific x-ray beam shapes.

Figure 15A:
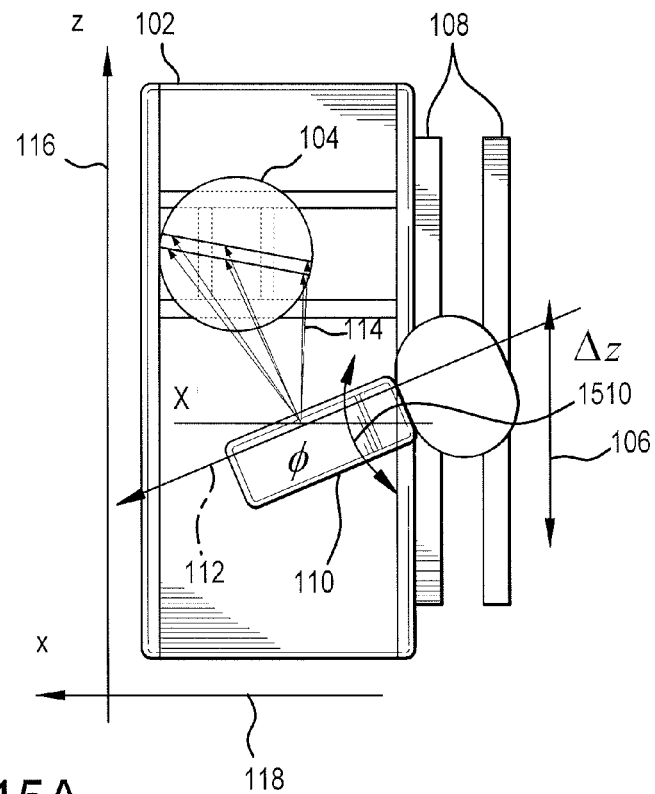
FIG. 15A illustrates rotation of an x-ray column with respect to a rotation axis, in accordance with one embodiment.
Figure 15B:
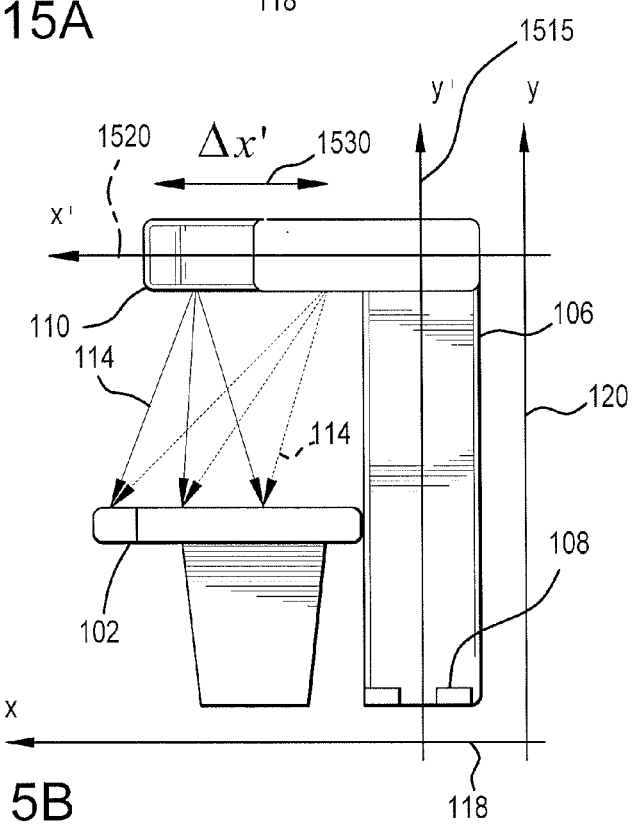
FIG. 15B illustrates motion of an x-ray beam along an axis parallel to a long axis of an x-ray tube, in accordance with one embodiment.
Figure 15C:
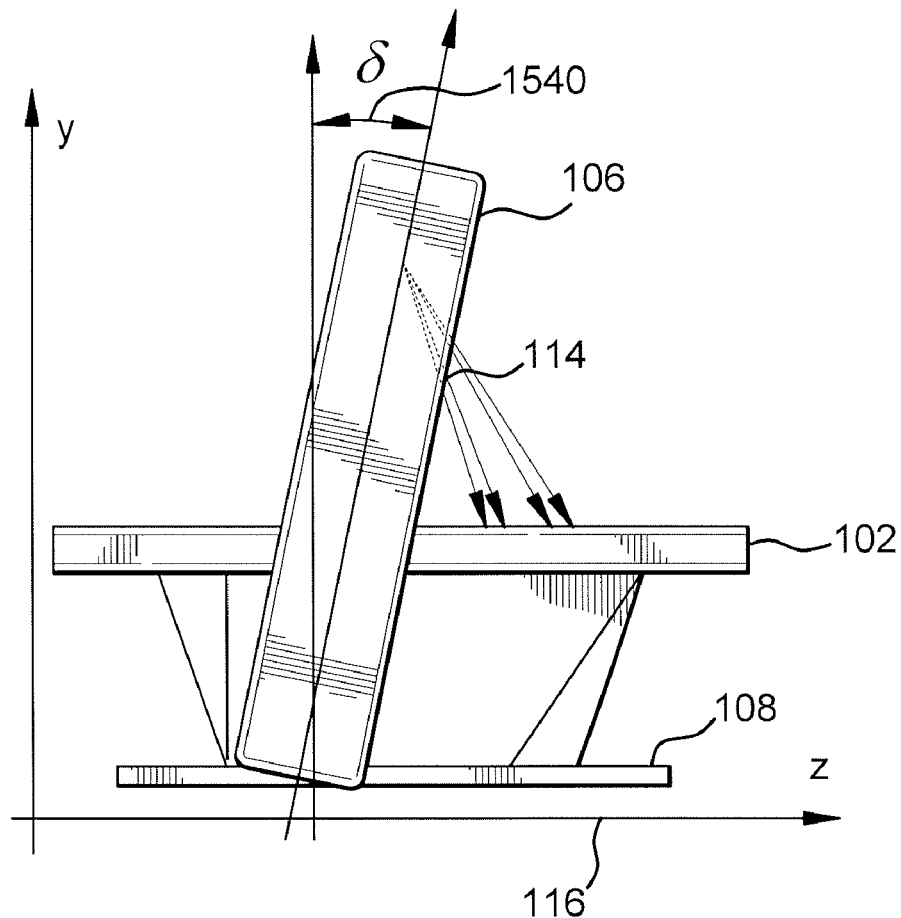
FIG. 15C shows rotation of an angle $\delta$ of an x-ray column, in accordance with one embodiment.

FIGS. 15A-15C schematically present a set of detector motions with respect to a number of axes. Tomosynthesis or limited-angle tomographic imaging may be enabled by moving a detector of specific shape along motion axes of FIGS. 15A-15C, while simultaneously moving the x-ray source along motion axes of FIGS. 15A-15C and shaping an x-ray beam to track the location and motion of the detector. Alternately, one or both of the x-ray source and detector may remain stationary during all or part of the imaging sequence. Where both the source and detector are stationary, an object to be imaged may move through an x-ray beam emitting from source to detector. For example, an object such as a suitcase moving along a conveyor belt may pass through the beam generated by stationary column assembly 106. Such an embodiment may find particular use in security screening applications, such as airport security or customs inspections.

In particular, FIG. 15A illustrates rotation of x-ray tube column assembly 106 by an angle φ 1510 with respect to rotation axis y' 1515 shown in FIG. 15B. FIG. 15B in turn presents motion of tube column assembly 106 along axis x' 1520 essentially including the x-ray tube 110 long axis. A displacement Δx' 1530 enables acquisition of a multiplicity of projections at various angles. Column assembly 106 (or x-ray tube 110) may rotate to track motion of an associated detector, e.g., detector 200. Alternately, column assembly 106 may remain stationary while detector 200 rotates, for example upon tray 204. In another embodiment, for example as described above with respect to airport security, above, both column assembly 106 and detector 200 center 212 remain stationary while a subject or object to be imaged moves through a rotating x-ray beam.

FIG. 15C illustrates rotation of angle δ 1540 of column assembly 106. This motion may also enable acquisition of a multiplicity of projections at various view angles; a similar effect may be enabled by translating x-ray tube 110 along z axis 116, as might be possible through rolling of the entire column 106 in this direction.

OPERATION

In one embodied mode of operation, the detector performs an initial "scout" scan of either the entire table or of a sub-area as prescribed by the user. Based on this initial scout image, the user or the system computer prescribes an area to be imaged. A number of imaging modes are possible, including linear raster scan of the area (possibly including a multiplicity of raster scan lines), or a combination of translation of the detector tray rotation axis O' together with continuous rotation of the detector around rotation axis y'.

In a second embodied mode of operation, the system is set to track the progress of an interventional tool, such as the tip of a catheter or other interventional device. The system automatically selects the detector tray center O' position so that the projection of the device tip is superimposed with the detector center O'. These automatic motions may be achieved either with or without simultaneous x-ray column translation along the subject table and associated x-ray tube pivoting with respect to axis x', depending on the imaging mode selected. Once the device tip has reached the theatre of operation (such as the coronary arteries in a cardiology procedure), the detector continues rotation around O', while minor adjustments to the O' location are dynamically made to maintain the device tip at image or detector tray center. The point O' may also be held at a given position, while fluoroscopic image refresh occurs through the continuous acquisition of data by the rotating detector. Alternatively, the detector trajectory may not include rotation, but be limited to a sequence of scans along specific raster lines, with the detector main axis either orthogonal or at a non-90-degrees angle with respect to the scan direction.

In another embodied mode of operation, adjustment of various system parameters, including relative position of the x-ray tube apparatus with respect to the object and detector, allow dynamically acquisition of several images of the same object for various projection angles and projection geometries. The projections may be chosen dynamically by the user, or the system may automatically loop through a pre-determined sequence of projections.

Dynamic operation of the system may also enable acquisition of image data at different levels of image noise, spatial resolution or spectral composition. In particular, the system may first be operated at a first level of resolution, noise, spectral composition or other imaging parameter, and then be switched to a higher resolution or reduced noise mode or different spectral composition, for example upon user or automatic detection of an abnormality or threat. Imaging acquisition may also take place at various levels of resolution, either dynamically in time or spatially; such various resolution and noise levels being for instance achieved through variable binning of the native resolution detector pixels. The various detector lines or arrays may have variable native pixel resolution as a function of the line or as a function of distance from detector iso-center.

The present instrumentalities may be applied to the operation of flat-panels area detectors, either specifically designed or operated as follows: A beam of specific shape and spectral characteristics is swept across the active surface of the detector. In one embodiment, a fan-beam is scanned linearly and/or rotated using a collimator assembly and methods according to the principles described herein. In another embodiment, a beam of more complex shape (such as may be formed by a collimator plate as described above) and/or containing several fans and a central area, is scanned linearly and/or rotated. The flat-panel data are read out to allow image formation and image refresh at rates depending on the spatial location of a given image pixel.

The present instrumentalities further apply to the operation of computed tomography (CT) systems, either specifically designed or operated as follows: A beam of specific shape and spectral characteristics is swept across the active surface of the detector, as described in the paragraph above. The beam sweeping may occur independently or simultaneously with gantry rotation.

In all embodiments where the detected x-ray beam is under-collimated with respect to the active detector, detector cells that are not exposed by the primary beam or by the beam penumbra detect scattered radiation. These measurements may be leveraged to perform scatter correction and or further object analysis and characterization.

Full-frame sampling of the active detector allows closed-loop dynamic adjustments to the x-ray beam parameters, including peak kilo-voltage, tube current, tube target location and selection, and filtration, to adapt x-ray imaging parameters to the composition of the object or anatomy being imaged.

In a tomosynthesis or limited-angle tomographic imaging mode, the x-ray source is set in motion along at least one of axes z 116 (column rolling), x' 1520 (tube translation along tube main axis), rotation of angle φ 1510 with respect to y' 122, or rotation of angle δ, 1540, or any motion that similarly contributes to the acquisition of a multiplicity of views (or projections) of the object to be imaged. Given the dynamics of the x-ray tube and the dynamics of the detector, the tracking algorithm orients tube angle (rotation with respect to the axis x') and/or collimator position and orientation, such that an x-ray beam of the appropriate shape projects onto the active part of the detector. This sequence of data acquisition results in the obtaining of a multiplicity of projection data that are then input to the 3D image reconstruction algorithm. A 3D image sequence can then be refreshed with the newly reconstructed information. Thus the system is designed for a fourth-dimensional data acquisition (time varying 3D data sets).

The advantages of the above described apparatus embodiments, improvements, and methods should be readily apparent to one skilled in the art, as to enabling the design of low-dose dynamic x-ray imaging systems and low-dose tomosynthesis and limited-angle computed tomography. Additional design considerations may be incorporated without departing from the spirit and scope of the invention. It should thus be noted that the matter contained in the above description and/or shown in the accompanying drawings should be interpreted as illustrative and not in a limiting sense. Accordingly, the following claims are intended to cover all generic and specific features described herein, as well as all statements of the scope of the present methods, and systems which, as a matter of language, might be said to fall therebetween.

What is claimed is:

1. A method for dynamic x-ray imaging of a subject or part of a subject, comprising:
   moving a detector tray supporting a detector having a non-circular shape by rotating the detector tray about an axis of rotation, co-aligned with a central axis of an x-ray beam, such that a greater density of detector cells of the detector are positioned at or near a center of the axis of rotation to provide greater x-ray detection area near the axis of rotation as compared to detector cells off-axis;
   shaping an x-ray beam to generally match the shape or part of the shape of the detector; and
   moving or orienting the x-ray beam to track the motion of the detector.

2. The method of claim 1, further comprising translating the detector tray.

3. A system for dynamic x-ray imaging of a subject or part of a subject, comprising:
   a gantry to rotate an x-ray detector of non-circular shape about an axis of rotation, co-aligned with a central axis of an x-ray beam, such that a greater density of detector cells of the detector are positioned at or near a center of the axis of rotation to provide greater x-ray detection area near the axis of rotation as compared to detector cells off-axis; a collimator to shape an x-ray beam to generally match the shape or part of the shape of the x-ray detector; and
   a beam orientation mechanism to track the motion of the detector with the x-ray beam.

4. The system of claim 3, wherein the detector gantry translates within a plane or curved surface.

5. The system of claim 3, comprising means for power and signal transmission between the rotating detector and a non-rotating supporting assembly.

6. The system of claim 3, wherein the detector of non-circular shape is mounted on a rotatable detector tray and the rotatable detector tray is mounted on a non-rotatable detector assembly that is moveable along at least two dimensions of a surface.

7. The system of claim 6, the non-rotatable detector assembly comprising a slip-ring assembly for transmitting power to the rotatable detector tray while not limiting the number of detector rotations.

8. The system of claim 6, wherein the detector assembly comprises a wireless transmitter and receiver for transmission from the rotatable detector tray to the non-rotatable rotatable detector assembly.

9. The system of claim 3, wherein the detector cells are arranged on a rectangular elongated matrix.

10. The system of claim 6, wherein the detector cells are arranged on a rectilinear elongated matrix and wherein additional detector cells are provided at or near a center of rotation of the detector tray to provide the greater x-ray detection area near the axis of rotation.

11. The system of claim 3, wherein the detector cells are arranged on a rectangular elongated matrix and wherein additional detector cells are provided on one or several additional matrices.

12. The system of claim 3, further comprising means to dynamically and automatically track the location of a point in space.

13. The system of claim 12, wherein the point in space corresponds to a point on an interventional medical device selected from the group of a catheter, brachytherapy seed, ablation element, sheath, probe and guide wire.

14. The system of claim 3, wherein the collimator is rotatable around the x-ray beam central axis.

15. The system of claim 3, comprising means for rotating the x-ray detector around the x-ray beam central axis in synchronicity with the collimator.

16. The system of claim 3, wherein the system is constructed and arranged for operation in a plurality of selectable imaging states including a tomosynthesis state and a non-tomosynthesis state.

17. The method of claim 1, shaping an x-ray beam comprising controlling shape of a collimator aperture using one or more of:
   an aperture plate; and
   at least one collimator blade.

* * * * *